US006323354B1

(12) United States Patent
Moore

(10) Patent No.: US 6,323,354 B1
(45) Date of Patent: Nov. 27, 2001

(54) AMINO ACID CHELATES FROM LIPOPROTEINS

(75) Inventor: William P. Moore, Hopewell, VA (US)

(73) Assignee: Agri-Nutrients Technology Group, Inc., Disputanta, VA (US)

( * ) Notice: Subject to any disclaimer, the term of this patent is extended or adjusted under 35 U.S.C. 154(b) by 0 days.

(21) Appl. No.: 09/808,887

(22) Filed: Mar. 16, 2001

(51) Int. Cl.[7] .............................. C07F 3/06; A61K 31/28; A23L 1/304
(52) U.S. Cl. .............................. 556/134; 556/50; 556/63; 556/116; 556/148; 554/8; 514/492; 514/499; 514/501; 514/502; 514/494; 514/505; 426/74
(58) Field of Search .................... 556/63, 50, 116, 556/134, 148; 554/8; 426/74; 514/492, 494, 499, 501, 502, 505

(56) References Cited

U.S. PATENT DOCUMENTS

| | | | | |
|---|---|---|---|---|
| 3,925,433 | * | 12/1975 | Abdel-Monem et al. | 260/438.5 R |
| 3,941,818 | * | 3/1976 | Abdel-Monem | 260/429.9 |
| 3,950,372 | * | 4/1976 | Abdel-Monem | 260/429 R |
| 3,969,540 | * | 7/1976 | Jensen | 426/657 |
| 4,021,569 | * | 5/1977 | Abdel-Monem | 424/289 |
| 4,067,994 | * | 1/1978 | Anderson et al. | 424/295 |
| 5,698,724 | * | 12/1997 | Anderson et al. | 556/50 |
| 5,846,581 | * | 12/1998 | Catron | 426/74 |
| 6,166,071 | * | 12/2000 | Ashmead et al. | 514/494 |
| 6,255,287 | * | 7/2001 | Watson et al. | 514/23 |

* cited by examiner

*Primary Examiner*—Porfirio Nazario-Gonzalez

(57) ABSTRACT

A method of preparing amino acid transition metal chelates a palatable highly bioavailable source of transition metals for animal nutrition from lipoproteins and transition metal salts. The method requires strong aqueous base hydrolysis of the lipoproteins to sodium or potassium salts of alpha amino acids mixed with fatty acids. The salts are neutralized to amino acids mixed with fatty acids before the aqueous mixture is reacted with transition metal salts to form aqueous chelates. The aqueous mixture is dried and granulated to form a dry product comprising transition metal chelates homogeneously mixed with fatty acids. The new granular composition containing zinc, iron, manganese, copper, cobalt, or chromium provides a palatable and highly bioavailable source of transition metals for animal nutrition. Effective sources of lipoproteins are fractured cell walls of microbes generated in biological syntheses.

15 Claims, No Drawings

AMINO ACID CHELATES FROM LIPOPROTEINS

BACKGROUND OF THE INVENTION

1. Field of the Invention

The present invention relates to minerals used for animal nutrition. More particularly, it relates to a method of converting lipoproteins and transition metal salts to transition metal amino acid chelates and fats; and also the products made by the method. The method comprises: the base hydrolysis of the lipoproteins to sodium or potassium salts of alpha amino acids mixed with fatty acids; neutralization of the salts to acids; and reaction of the alpha amino acids with soluble salts of the transition metals to form chelates mixed with fatty acids.

2. Description of Related Art

The transition metals have been recognized for many years as important trace minerals for maintaining health and good nutrition in animals. The Official Publication, 1996, Association of American Feed Control Officials (AAFCO) recognizes and defines such products as item "57.142 Metal Amino Acid Chelate. The Product resulting from the reaction of a metal ion from a soluble metal salt with amino acids with a mole ratio of one mole of metal to one to three (preferably two) moles of amino acid to form coordinate covalent bonds. The total molecular weight of the hydrolyzed chelate must not exceed 800."

In U.S. Pat. No. 5,698,724, Anderson et al disclose a method of preparing a metal amino acid complex from protein starting material by strong acid hydrolysis of protein to provide an amino acid hydrolyzate in about 1 to 3 hours at elevated temperature and pressure. Metal oxide is then added to the amino acid hydrolyzate to form a metal amino acid complex. Anderson et al use a strong inorganic acid at the high concentration of 6 normal, which is then neutralized to a pH of 4 to 5 by addition of alkali or alkaline earth hydroxide.

U.S. Pat. Nos. 3,925,433, Abdel-Monem et al; 3,941,818, Abdel-Monem; 3,950,372, Abdel-Monem; 4,021,569, Abdel-Monem; and 4,067,994, Anderson et al teach preparation of 1:1 complexes of alpha amino acids, preferably methionine, and transition metals. These complexes are 1:1 complex salts prepared from pure amino acids. The foregoing patents refer to complexes and not to chelates. Complexes are not necessarily chelates, but chelates are considered to be special ring structured metal complexes.

Ned L. Jensen in U.S. Pat. No. 3,969,540 taught a method of preparing metal proteinates consisting of metal chelates of polypeptides using enzymatic hydrolysis so that the chelates are substantially free from metal salts and from single amino acid proteinates.

None of the foregoing references provide for the base hydrolysis of lipoproteins into an aqueous mixture of sodium or potassium salts of alpha amino acids and fatty acids, followed by the reaction of the aqueous mixture with transition metal salts to form a palatable mixture of transition metal amino acid chelates mixed with fatty acids.

Many of the proteinacious materials economically available as by-products or wastes are lipoproteins containing substantial amounts of fats or lipid groups conjugated with protein groups into long chain polymers. These lipoproteins are resistant to hydrolysis by enzymatic or acid hydrolysis. Further, the lipids when treated with strong acids, such as sulfuric acid, at elevated temperatures char, making the resultant product unpalatable to animals.

In this disclosure "lipoprotein" means lipids, or fats, or fatty acid groups conjugated with protein and, or amino acid groups into polymeric structures. Lipoproteins are found in most animal generated proteins, including, single cell proteins, fermentation solids, and biological process by-products where microbes are cultivated to produce a particular chemical such as lysine or other amino acids.

Transition metals have varying degrees of chelate forming stability with chelating agents, and the stabilities of the metals vary with any given chelating agent. When the term "transition metals" is used herein it means zinc, copper, manganese, iron, cobalt, copper and magnesium, as a group or as individual metals.

The term "biosynthesis" is used herein to mean the synthesis of desired chemical compounds by the use of particular strains of microbes which have the ability to convert raw materials, such as ammonia, sugar, and water by catalytic action to products such as alpha amino acids. The biosyntheses always leaves a by-product of fractured cell walls from the dead microbes on completion of the process.

The term "conventional means of drying" herein means drying a product by ordinary drying methods in use commercially, such as by fluid bed, rotary drum, steam tube, spray, or tray dryer.

Bioavailability of the transition metals is defined as the portion of the metal which is absorbed, transported to its site of action, and converted to a physiologically active form—the availability of the metal for use by the consuming animal.

It is a primary object of this invention to provide a method of preparing amino acid transition metal chelates as a palatable bioavailable source of transition metals for animal nutrition from lipoproteins and transition metal salts.

It is another object of this invention to provide a method of preparing these chelates from biological and agricultural industry by-products such as solids recovered from fermentation processes, solid single cell feed proteins from biosynthesis from hydrocarbons or alcohols, solids recovered from biosynthesis of organic chemicals and from blood meal, fish meal and other meals of animal origin.

It is still another object to produce a palatable bioavailable transition-metal amino acid chelate-fatty acid composition for animal nutrition.

SUMMARY OF THE INVENTION

I have now discovered a method of preparing amino acid transition metal chelates homogeneously mixed with fatty acids which are a highly bioavailable and palatable source of transition metals for animal nutrition from lipoproteins and transition metal salts. It was found that the method is only effective when an aqueous lipoprotein is hydrolyzed with strong sodium or potassium base until aqueous sodium or potassium salts of amino acids and fatty acids are formed. The salts are then neutralized to amino acids mixed with fatty acids, and the amino acid-fatty acid mixture is reacted with water soluble salts of transition metal ions so that between 1 and 3 molecules of amino acid are provided per transition element ion, thereby forming amino acid transition element chelate homogeneously mixed with fatty acids.

It was found that the amino acid chelates prepared by the foregoing aqueous method could be dried into stable, attrition resistant granules, which provided highly bioavailable and palatable sources of transition metal ions.

DESCRIPTION OF THE INVENTION

In the instant invention a new method is provided for preparing transition metal amino acid chelates mixed with fatty acids as bioavailable and palatable animal feed minerals from lipoproteins by strong base hydrolysis to sodium or potassium salts of amino acids and fatty acids, followed by the chelating reaction with water soluble transition metal salts.

In the method of preparing amino acid transition metal chelates which are palatable and highly bioavailable sources of transition metals for animal nutrition from lipoproteins and transition metal salts, it is necessary to admix a sodium or potassium base with an aqueous lipoprotein, and hydrolyze the lipoprotein at a temperature between 90 and 180° C. at pH higher than 9 until aqueous sodium or potassium salts of amino acids and fatty acids are formed. Other bases such as alkaline earths are ineffective because of strong interference with the formation of the desired transition metal chelates later in the procedure.

To effectively form the chelate, it is necessary to neutralize the aqueous sodium or potassium salts of the amino acids and fatty acids to a pH between 3 and 7. Then, the water soluble salts of transition metals may be reacted with the neutralized sodium or potassium salts of amino acids and fatty acids to provide between 1 and 3, and preferably between 1.8 and 2.5 molecules of amino acid per transition metal, thereby forming an aqueous mixture of amino acid transition metal chelates and fatty acids.

To provide optimum stability of the transition metal chelates, the pH of the aqueous mixture of amino acid transition metal chelates and fatty acids is adjusted to between 4.5 and 7.5 by additions of small amounts of acids or bases as necessary.

The transition metals found to be effective in the instant method of forming amino acid chelates include zinc, copper, manganese, magnesium, iron, cobalt and chromium.

Lipoproteins which may be used effectively in the instant method are biological process and agricultural industry by-products including solids recovered from fermentation processes, solid single cell proteins resulting from biosynthesis from hydrocarbons or alcohols, solids recovered from biosynthesis of organic chemicals, blood meal, fish meal, and other meals of animal origin.

A particularly effective source of lipoproteins in the instant method is the fractured cell walls from the microbes generated in the biological synthesis of amino acids, using specific strains of microbes to produce specific amino acids, such as proline cystein, alanine, valine, lysine, leucine and isoleucine. The fractured cell walls are recovered by filtration or centrifugation after extraction of the amino acid products.

It was found that a wide range of lipoproteins could be used in the instant method. The lipoproteins need not be pure but may comprise a part of a mixture of protein and protein-like materials. Some of the materials which contain lipoprotein mixtures but may be used effectively are nucleoproteins, nucleic acids, keratins, collagen, and hemoproteins The instant method operates most effectively when the hydrolyzing of the lipoproteins is performed in a dilute aqueous solution containing between 5 and 15 percent crude protein.

The method is also most effectively carried out when the lipoprotein contains between 3 and 7 parts by weight crude protein per part of fat. The crude protein is calculated by multiplying the nitrogen content by 6.25, and the fat is determined by the AOAC solvent extraction method. Higher fat content slows the hydrolysis process and undesirably dilutes the final chelate metal content.

The lipoprotein is preferably hydrolyzed at a temperature between 120 and 150° C. at a gage pressure between 20 and 40 pounds per square inch. It was found that temperatures below 120° C. produced undesirably slow hydrolysis and that temperatures above 150° C. caused conversion of appreciable amounts of lipoproteins to ammonia. The pressures were required to provide the necessary temperatures in the aqueous mixtures.

To neutralize the aqueous sodium or potassium salts of amino acids and fatty acids to a pH between 4 and 6, it was preferred to admix one or more of the following acids: sulfuric, hydrochloric, acetic, and citric.

Although the aqueous mixture of amino acid transition metal chelates and fatty acids may be used as effective sources of chelates for animal nutrition, the metal concentration is necessarily low. To facilitate utility, it is necessary that the aqueous mixture of amino acid transition metal chelates and fatty acids is dried by conventional means to form solid particles comprising between 85 and 99.5 percent dry matter, between 3 and 15 percent transition metal, and between 7 and 46 percent crude protein.

The amino acid transition metal chelate-fatty acid composition prepared by the instant method provides a highly bioavailable and palatable source of transition metals for animal nutrition.

A particularly effective aspect of the instant invention is the method of preparing alpha amino acid transition metal chelates mixed with fatty acids which exhibit bioavailability and palatability as animal feed ingredients from lipoproteins comprising fractured cell walls of microbes grown in biological synthesis of alpha amino acids, and transition metal salts.

In this aspect of the invention, sodium hydroxide is admixed with an aqueous lipoprotein emulsion comprising fractured cell walls of microbes generated in biological synthesis of alpha amino acids. The fractured cell walls are recovered by centrifuging, settling or filtering after extraction of the alpha amino acids from the microbes.

The admixed sodium hydroxide and aqueous lipoprotein emulsion are heated to a temperature between 130 and 145° C. until the lipoprotein is hydrolyzed to form an aqueous mixture of sodium salts of alpha amino acids and fatty acids.

The method is effective when the aqueous mixture of sodium salts is neutralized to a pH between 4.5 and 6.0 by admixing sulfuric acid.

Although acid salts may be used to make the chelate and eliminate the neutralizing step, it is preferred to accurately neutralize in a separate step before the chelate is made.

In the preferred method, water soluble sulfate salts of transition metal are admixed with the neutralized aqueous mixture of sodium salts of alpha amino acids and fatty acids to provide between 1.9 and 2.3 molecules of alpha amino acid nitrogen per transition metal ion, thereby forming an aqueous mixture of alpha amino acid transition metal chelates and fatty acids, the transition metal found most effective being iron, manganese, zinc, copper, magnesium, cobalt, and chromium.

To put the product in best condition for use, the aqueous mixture of alpha amino acid transition metal chelate and fatty acids is dried by conventional means to form granules comprising between 95 and 99 percent dry matter, between 8 and 13 percent transition metal, between 20 and 30 percent crude protein, and between 3 and 10 percent fatty acids.

It was found that the alpha amino acid transition metal chelate mixed with fatty acid composition prepared by the foregoing method comprised a highly bioavailable and palatable source of transition metals, protein, and fat for animal nutrition.

PREFERRED EMBODIMENT OF INVENTION

The following examples are provided to illustrate the preferred embodiments of the invention.

EXAMPLE 1

This example demonstrates the effectiveness of the method of converting lipoproteins and soluble transition metal salts to chelates mixed with fatty acids, using fractured microbe walls as the source of lipoproteins and zinc sulfate as the source of soluble transition metal salts.

Fractured microbe cell wall by-product, from the commercial scale biosynthesis of proline using a specific strain of microbes was recovered by filtration and by settling as a dilute aqueous emulsion. The aqueous mixture was obtained by recovery of the fractured cell walls after extraction of the proline and also from the equipment wash down after the completion of the proline production run. The composition of the combined stream amounting to 61,600 pounds is listed as follows:

| Components | Wt % |
|---|---|
| Moisture | 90.72 |
| Fat | 1.22 |
| (Nitrogen) | 0.96 |
| Protein | 6.00 |
| Dry Matter | 9.28 |

The aqueous lipoprotein was charged to a Hydrolysis Tank fitted with a steam jacket and stirrer and equipped for pressure operation. To the Hydrolysis Tank was added 5,544 pounds of strong caustic soda (50.0% NaOH).

The mixture was heated for 8 hours at a temperature between 130–136° C. at a pressure between 28 and 35 psig. During this reaction time, the lipoprotein was hydrolyzed into soluble sodium salts of a mixture of amino acids and fatty acids providing a low viscosity solution amounting to 67,144 pounds. Analysis of the hydrolyzate was as follows:

| Component | Wt % |
|---|---|
| Moisture | 94.00 |
| Fatty Acid Salts (as fat) | 1.12 |
| Amino Acid Salts (as protein) | 5.50 |
| Dry Matter | 12.65 |

The pH of the hydrolyzate was 10.1 and it was neutralized to a pH of 5 by adding 3,539 pounds of 98.0 percent sulfuric acid. Then 4,276 pounds of zinc sulfate fines, containing 36 percent zinc, 17 percent sulfur, and 17 percent moisture was added and mixed for 15 minutes forming an aqueous solution of zinc amino acid chelate mixed with fatty acids. Cooling was applied to the reactor tank during the neutralization and chelate forming steps to maintain a temperature of 40 to 43° C. during the operations. The aqueous product was analyzed to show the following composition:

| Component | Wt % |
|---|---|
| Moisture | 78.91 |
| Fatty Acids (as fat) | 1.00 |
| Amino Acid Zinc Chelate (as protein) | 4.91 |
| Amino Acid Zinc Chelate (as zinc) | 2.06 |
| Dry Matter | 21.09 |

The aqueous product was dried in a fluid bed dryer, using a 3/1 recycle of dry product, operating with a 205° C. inlet air temperature and a 82° C. product discharge temperature. The product amounting to 16,129 pounds was cooled to 32° C. and recovered in super sacks with analysis as follows:

| Component | Wt % |
|---|---|
| Fatty Acids (as fat) | 4.64 |
| Amino Acid Zinc Chelate (as protein) | 22.80 |
| Amino Acid Zinc Chelate (as zinc) | 9.55 |
| Moisture | 2.00 |
| Dry Matter | 98.00 |

The molecular ratio of amino acid nitrogen to zinc was 1.77.

EXAMPLE 2

This example demonstrates that the zinc amino acid compound formed is a zinc chelate by comparing its resistance to precipitation compared to zinc sulfate when titrated with sodium hydroxide in water solution.

A one-gram sample of the granular product of Example 1 was accurately weighed and thoroughly mixed with 50 ml of distilled water in a stirred beaker equipped with a pH probe capable of accurately measuring pH of the beaker contents. With constant stirring 0.1 normal sodium hydroxide was slowly added with pH recorded after each 0.1 ml sodium hydroxide added. A summary of the titration data is provided in the following table.

| 0.1N NaOH, ml | pH of Example 1 Sample |
|---|---|
| 0.0 | 5.1 |
| 2.0 | 5.5 |
| 4.0 | 6.0 |
| 8.0 | 6.9 |
| 10.0 | 7.2 |
| 16.0 | 8.5 |
| 20.0 | 9.2 |

No precipitation of zinc as zinc hydroxide occurred as the sodium hydroxide was added. When an identical titration of the same amount of zinc in pure zinc sulfate was made in 50 ml of distilled water, the zinc precipitated from the zinc sulfate as zinc hydroxide as sufficient 0.1 normal sodium hydroxide was added to increase pH to 3.5 The degree of protection from precipitation of the zinc provided by the chelate is indicated by the pH which the liquid may be increased to without the zinc precipitating.

EXAMPLE 3

This example demonstrates the palatability of the chelates of the instant invention.

The product of Example 1, containing 9.55 weight percent zinc was fed at a rate of 1.8 grams of product per head per day to feedlot beef cattle with no sign of feed rejections. A still higher feed rate of 4.0 grams of product was fed to a lactating dairy herd with good palatability of the feed containing the chelate product observed.

EXAMPLE 4

This example demonstrates the bioavailability and efficacy of the chelates of the instant invention in optimizing the amount of milk production in a dairy herd.

The zinc chelate of Example 1 was fed to a large dairy herd at a rate of 1.8 grams per head of dry cows per day and 4.0 grams per head of lactating cows per day throughout a two-year test period. The average number of open days per cow in the test herd was compared to the average number of open days in the control herd receiving the same amount of zinc in the form of zinc sulfate. The following table summarizes the test results comparing the results with the zinc chelate of Example 1 and zinc sulfate with regard to the number of open days when the cows are not producing milk.

| Zinc Source | Open Days | Decrease in Open Days, % |
| --- | --- | --- |
| Zinc Sulfate | 118 | — |
| Zinc Chelate (Example 1) | 95 | 19.5 |

EXAMPLE 5

This example demonstrates the preparation of amino acid chelates from the transition metals zinc, copper, manganese, cobalt and ferrous iron.

The hydrolyzate of Example 1 was neutralized to a pH of 5.5 by addition of sulfuric acid and then the following salts were added with vigorous stirring at ambient temperature: zinc sulfate, copper sulfate, manganese sulfate, ferrous sulfate, and cobalt sulfate, using an overall ratio of 2.1 moles of amino acid nitrogen per mole of transition metal.

The product was granulated and dried by the method of Example 1 and analyzed to provide the following composition:

| Component | Wt % |
| --- | --- |
| Amino Acid Chelate as Zinc | 4.40 |
| Amino Acid Chelate as Manganese | 2.40 |
| Amino Acid Chelate as Copper | 1.51 |
| Amino Acid Chelate as Cobalt | 0.31 |
| Amino Acid Chelate as Iron | 0.20 |
| Amino Acid Chelate as Protein | 26.37 |
| Fatty Acids (as fat) | 5.40 |
| Moisture | 1.90 |
| Dry Matter | 98.10 |

I claim:

1. A method of preparing amino acid transition metal chelates, a palatable highly bioavailable source of transition metals for animal nutrition, from lipoproteins and transition metal salts, the method comprising:
   (a) admixing a sodium or potassium base with an aqueous lipoprotein, and hydrolyzing the lipoprotein at a temperature between 90 and 180° C. at a pH higher than 9 until aqueous sodium or potassium salts of amino acids and fatty acids are formed;
   (b) neutralizing the aqueous sodium or potassium salts of amino acids and fatty acids to a pH between 3 and 7; and,
   (c) reacting water soluble salts of transition metals with the neutralized sodium or potassium salts of amino acids and fatty acids to provide between 1 and 3 molecules of amino acid per transition metal ion, thereby forming an aqueous mixture of amino acid transition metal chelates and fatty acids.

2. The method of claim 1 wherein the pH of the aqueous mixture of amino acid transition metal chelates and fatty acids is adjusted to between 4.5 and 7.5 by additions of acids or bases to provide optimum stability of the transition metal chelates.

3. The method of claim 1 wherein the transition metals are selected from the group consisting of zinc, copper, manganese, magnesium, iron, cobalt, and chromium.

4. The method claim 1 wherein the lipoproteins comprise biological and agricultural industry by-products selected from the group consisting of: solids recovered from fermentation processes, solid single cell feed proteins from biosynthesis from hydrocarbons or alcohols, solids recovered from biosynthesis of organic chemicals, blood meal, fish meal, and other meals of animal origin.

5. The method of claim 1 wherein the lipoproteins comprise fractured cell walls of microbes generated in biological synthesis of amino acids, the fractured cell walls being recovered after the extraction of the amino acid products from the fractured cells.

6. The method of claim 1 wherein the lipoproteins comprise a part of a mixture of protein and protein-like materials selected from the group consisting of nucleoproteins, nucleic acids, keratins, collagen, hemoproteins, and glutamic acid.

7. The method of claim 1 wherein the hydrolyzing of the lipoproteins is performed in a dilute aqueous solution containing between 5 and 15 percent crude protein.

8. The method of claim 1 wherein the lipoprotein contains between 3 and 7 parts by weight of protein per part of fat.

9. The method of claim 1 wherein the lipoprotein is hydrolyzed at a temperature between 120 and 150° C. at a gage pressure between 20 and 40 pounds per square inch.

10. The method of claim 1 wherein the aqueous sodium or potassium salts of amino acids and fatty acids are neutralized to a pH between 4 and 6 by admixing an acid selected from the group consisting of: sulfuric, hydrochloric, acetic, and citric.

11. The method of claim 1 wherein the water soluble salts of transition metal ions admixed with the neutralized sodium or potassium salts of amino acids and fatty acids provide one transition metal ion for between 1.8 and 2.5 molecules of amino acid nitrogen.

12. The method of claim 1 wherein the aqueous mixture of amino acid transition metal chelates and fatty acids is dried by conventional means to form solid particles comprising between 85.0 and 99.5 percent dry matter, between 3 and 15 percent transition metal, and between 7 and 46 percent crude protein.

13. An amino acid transition metal chelate-fatty acid composition which provides a highly bioavailable and palatable source of transition metals for animal nutrition, prepared by the method of claim 1.

14. A method of preparing alpha amino acid transition metal chelates mixed with fatty acids, which exhibit bioavailability and palatability as animal feed ingredients, from lipoproteins comprising fractured cell walls of microbes grown in biological syntheses of alpha amino acids, and transition metal salts, the method comprising:

(a) admixing sodium hydroxide with an aqueous lipoprotein emulsion comprising fractured cell walls of microbes generated in biological synthesis of alpha amino acids, the aim fractured cell walls being recovered by centrifuging, settling, or filtering after extraction of the alpha amino acids from the microbes;

(b) heating the admixed sodium hydroxide and aqueous lipoprotein emulsion to a temperature between 130 and 145° C. until the lipoprotein is hydrolyzed and an aqueous mixture of sodium salts of alpha amino acids and fatty acids is formed;

(c) neutralizing the aqueous mixture of sodium salts to a pH between 4.5 and 6.0 by admixing sulfuric acid therewith;

(d) admixing water soluble sulfate salts of transition metals with the neutralized aqueous mixture of sodium salts of alpha amino acids and fatty acids to provide between 1.9 and 2.3 molecules of alpha amino acid nitrogen per transition metal ion, thereby forming an aqueous mixture of alpha amino acid transition metal chelates mixed with fatty acids, the transition metal ions being selected from the group consisting of iron, manganese, zinc, copper, magnesium, cobalt, and chromium; and, (e) drying the aqueous mixture of alpha amino acid transition metal chelates and fatty acids by conventional means to form granules comprising between 95 and 99 percent dry matter, between 8 and 13 percent transition metal, between 20 and 30 percent crude protein, and between 3 and 10 percent fatty acids.

15. An alpha amino acid transition metal chelate and fatty acid composition comprising a highly bioavailable and palatable source of transition metals, protein, and fat for animal nutrition, prepared by the method of claim 14.

* * * * *